United States Patent
Upadhyaya et al.

(10) Patent No.: US 6,834,550 B2
(45) Date of Patent: Dec. 28, 2004

(54) SOIL PROFILE FORCE MEASUREMENT USING AN INSTRUMENTED TINE

(75) Inventors: Shrinivasa Upadhyaya, Davis, CA (US); Pedro Andrade-Sanchez, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/238,928

(22) Filed: Sep. 9, 2002

(65) Prior Publication Data

US 2003/0066357 A1 Apr. 10, 2003

Related U.S. Application Data

(60) Provisional application No. 60/322,365, filed on Sep. 10, 2001.

(51) Int. Cl.$^7$ ................................................ G01B 5/00
(52) U.S. Cl. ...................................................... 73/784
(58) Field of Search ........................... 73/784, 788, 794, 73/799, 818, 825, 84, 78, 79, 81, 85, 803

(56) References Cited

U.S. PATENT DOCUMENTS

| | | | | | |
|---|---|---|---|---|---|
| 3,673,861 | A | * | 7/1972 | Handy | 73/841 |
| 3,795,279 | A | * | 3/1974 | Nelson | 172/3 |
| 3,956,924 | A | * | 5/1976 | Hansen et al. | 73/81 |
| 4,815,342 | A | * | 3/1989 | Brett et al. | 76/108.2 |
| 5,461,229 | A | * | 10/1995 | Sauter et al. | 250/253 |
| 5,904,083 | A | * | 5/1999 | Jensen et al. | 83/62 |
| 5,950,141 | A | * | 9/1999 | Yamamoto et al. | 702/41 |
| 5,970,901 | A | * | 10/1999 | Bruce | 114/293 |
| 6,431,287 | B1 | * | 8/2002 | Ramp | 172/133 |

FOREIGN PATENT DOCUMENTS

DD      DD 274 486 A      12/1989

OTHER PUBLICATIONS

Glancey, James L. et al.; "Prediction of Agricultural Implement Draft Using an Instrumented Analog Tillage Tool," Soil & Tillage Research, vol. 37, pp. 47–65, (1996).

Glancey, James L. et al.; "An Instrumented Chisel for the Study of Soil–Tillage Dynamics," Soil & Tillage Research, vol. 14, pp. 1–24, (1989).

(List continued on next page.)

*Primary Examiner*—Max Noori
(74) *Attorney, Agent, or Firm*—John P. O'Banion

(57) ABSTRACT

A profile sensor and method for mapping the variability in soil compaction and soil characteristics with respect to depth. One embodiment of the apparatus includes a tine with a plurality of cutting elements supported by a plurality of independent load cells configured to measure the force exerted on the cutting elements as the tine is pulled through the soil of a field. Soil cutting forces through the soil profile are preferably measured to a depth of 63 cm in increments of 7.5 cm. The profile sensor showed that the cutting force is influenced by soil moisture content, depth of operation of the tine and vertical location of the cutting element.

63 Claims, 10 Drawing Sheets

OTHER PUBLICATIONS

Upadhyaya, S.K. et al.; "Precision Farming in a Tomato Production System," American Society Agricultural Engineering Meeting Presentation, Paper No. 99–1147, pp. 1 thru 19, Toronto, Ontario, Canada, Jul. 18–21, 1999.

ASAE Standards 1995: ASAE S313.2. "Soil Cone Penetrometer" pp. 486., ASAE, St. Joseph, MI 49085.

Lui, W. et al.; "Development of a Texture/Soil Compaction Sensor," Biological and Agricultural Engineering Department, UC Davis, pp. 1–14, (2000).

Andrade, Pedro et al.; "Soil Strength Dynamics Under Different Management Systems," American Society Agricultural Engineering Meeting Presentation, Paper No. 00–2156, pp. 1 thru 10, Midwest Express Center, Milwaukee, Wisconsin, Jul. 9–12, 2000.

Andrade, Pedro et al.; "Soil Profile Force Measurements Using an Instrumented Tine," Internet Article, Online, 2001, XP002229394, Written for presentation at the 2001 ASAE Annual International Metting, pp. 1 thru 5, Jul. 28, Aug. 1, 2001.

Lui, W. et al.; "Development of a Texture/Soil Compaction Sensor," Proceedings of Third International Conference on Precision Agriculture, XP001133771, pp. 617–630, Jun. 23, 1996.

Glancey, J.L.; "Prediction of Agricultural Implement Draught Using an Instrumented Analog Tillage Tool," Soil & Tillage Research, XP002229379, vol. 3537, pp. 47–65, (1996).

* cited by examiner

SOIL PROFILE FORCE MEASUREMENT USING AN INSTRUMENTED TINE

CROSS-REFERENCE TO RELATED APPLICATIONS

This application claims priority from U.S. provisional application Ser. No. 60/322,365 filed on Sep. 10, 2001, incorporated herein by reference.

STATEMENT REGARDING FEDERALLY SPONSORED RESEARCH OR DEVELOPMENT

Not Applicable

REFERENCE TO A COMPUTER PROGRAM APPENDIX

Not Applicable

BACKGROUND OF THE INVENTION

1. Field of the Invention

This invention pertains generally to precision farming implements and methods, and more particularly to an apparatus and method for determining, evaluating and analyzing soil profile force measurements using an instrumented tine.

2. Description of the Background Art

Efficient farm management has become even more important to the economic survival of farmers in recent years because of increases in capital investment, increases in operating costs, and growing environmental constraints. The impact of agricultural production on the environment from chemical runoff and soil erosion has lead to the adoption of conservation tillage and precision farming techniques by farmers. Proper use of conservation tillage and precision farming techniques may lead to a reduction of soil erosion, over-fertilization and excess watering as well as a reduction in energy input and production costs. Logically, greater profits may be achieved through increasing crop production or decreasing the costs of production.

The physical and chemical characteristics of the soil as well as environmental conditions are generally regarded as the main sources of variability in crop yield. Good plant growth is influenced by the exchange of air and water with plant roots. The structure of the soil affects the movement of plant roots, air and water through the soil and ultimately the productivity of the field. Stable groupings of particles of clay, sand, organic matter and silt form aggregates that provide a rough network of passages or channels that allow the free exchange of air and water with the roots of the plants. The stability of the soil structure may be influenced by the size and type of particles forming the aggregate, wetting and drying cycles, temperatures extremes, freezing and thawing, mechanical compaction and the presence of inorganic and organic cementing agents within the soil. Soil structure can also be adversely influenced by excessive cultivation and the tillage of wet soils.

The density and structure of the soil and the size and continuity of the spaces between particles comprising the soil determine the permeability of the soil to the movement of air and water. The ability of a soil to absorb irrigation water or rain over a specified period of time is dependent on the permeability of the surface soil, the moisture content of the soil and the slope of the field. Soils with very slow or very fast infiltration rates are generally considered to be poor soils for irrigation. In addition, a reduction of water infiltration and hydraulic conductivity within the soil profile due to soil compaction or crusting can contribute to runoff and erosion. Moreover, reduced infiltration rate and hydraulic conductivity leads to lower soil moisture status and poor yield.

In addition to adversely affecting the availability of soil moisture within the root zone, the possible serious, long-term effects of soil compaction on the quality of the environment has become a serious issue in recent years. Soil compaction may have a significant environmental effect in four general areas: atmosphere, surface water, ground water and soil vitality. Atmospheric effects of soil compaction are seen in the increased emission of greenhouse gases caused by anaerobic conditions present in moist and compact soils as well as emissions from machinery due to the need of increased tillage required for compact soils. Decreased infiltration in compact soils leads to increased runoff and the associated erosion and chemical runoff that may occur. Compacted soils result in reduced root growth and a decreased ability to absorb nutrients in a plant producing an increased need for fertilizer applications to maintain crop production. Ground water contamination by excessive fertilizer applications is a continuous environmental concern. Another adverse effect of soil compaction results in a reduction in the physical, chemical and biological quality of the soil such as decreased hydraulic conductivity and a loss of habitat for micro-fauna and macro-fauna in the soil.

Soil structure may deteriorate in many ways resulting from exposure to machinery traffic, a percentage decrease in the organic matter in the soil or through certain tillage practices. The severity of the compaction may vary depending on the soil type, crop type and soil moisture present in the field.

Soil compaction is typically monitored by the use of an ASAE (American Society of Agricultural Engineers) standard cone penetrometer providing a soil cone index value. Although cone index measurements provide variability in soil compaction through depth, they are point measurements that may be highly variable and may not be indicative of the conditions of the entire field.

In contrast, Texture/Compaction Index (TCI) sensor measures soil cutting force continuously over the entire tillage depth that provides a single measure of average soil compaction over the whole profile. However, this device can not provide variability in soil compaction level with depth which is critical for locating compact layers within the soil profile.

All of the aforementioned concerns point to the need for an analytical apparatus and method that can sense soil compaction status that will allow field management decisions including tillage depths and optimized soil particle sizes, crop selection, improve water infiltration characteristics, fertilization types and application rates and other precision farming decisions. Informed farming decisions and practices will reduce the input of energy and maximize the net return from the field. The present invention satisfies these needs, as well as others, as will be seen herein.

BRIEF SUMMARY OF THE INVENTION

The present invention is directed to an agricultural soil profile sensor apparatus and method for providing field position relevant measurements of soil compaction and other soil characteristics with respect to soil depth in real-time.

In general terms, the invention comprises a plurality of cutting elements and means for measuring force on each of the cutting elements as said cutting elements are pulled through soil.

According to another aspect of the invention, the apparatus comprises a tine having a plurality of cutting elements, and a plurality of independent load cells supporting said cutting elements on said tine wherein the load cells are configured for measuring force on each of the cutting elements as said cutting elements are pulled through soil.

In accordance with a still further aspect of the invention, the apparatus comprises a tine having a plurality of cutting elements, means for measuring soil resistance to cutting as said cutting elements are pulled through soil, and means for mapping the variability in soil resistance to cutting with respect to depth.

The invention also includes a method for measuring variability in soil compaction with respect to depth that generally comprises measuring soil resistance to cutting as a plurality of cutting elements are pulled through soil.

By way of example, and not of limitation, a profile sensor apparatus according to the present invention generally comprises a tine that is drawn vertically through the soil at depths of up to approximately 60 centimeters that provides a platform for a variety of sensors.

It has been shown that the physical and chemical characteristics of the soil as well as environmental conditions are generally the main causes of variability in crop yields. One of the most important soil characteristics is the variability in soil moisture status. Soil moisture variability is governed by poor soil infiltration characteristics which in turn are associated with an increased level of soil compaction and/or changes in soil texture. It will be seen that the cutting force exerted on the apparatus as it is pulled through soil is influenced by soil moisture content, depth of operation of the tine and the vertical location of the cutting element.

According to an aspect of the invention, the tine has a plurality of independent cutting elements that are configured to transfer forces onto load cells. Each edge provides cutting resistance information over, for example, a 7.5-centimeter layer in the soil profile to a total depth, for example, of 60 centimeters. Each layer has a 5 cm cutting element separated by a 2.5 cm dummy element. Each cutting element is preferably coupled to a load cell or other device for measuring force. The dummy elements serve to allow discrete layer measurements.

The tine may also have other sensors located above or below ground. For example, temperature sensors, depth sensors, moisture sensors, salinity sensors and field position sensors and the like may be used to provide additional data for a field profile over a growing season or in the short term. Additional sensors may also be located on the vehicle.

In use, the apparatus is drawn linearly through the subject field, and measurements of the mechanical impedance through different layers within the soil profile are preferably taken. In one embodiment, the soil force measurements are recorded by a data logger and stored for analysis away from the field. In another embodiment, the force measurements are stored and analyzed by a computer and the results displayed in real time. In another embodiment, the computer stores and compares previous measurements and data with the current measurements to disclose trends and improvements.

A map of the field at various depths may also be created from the obtained data and correlated surface positions within the field in one embodiment. Decisions regarding irrigation frequencies, fertilizer application, mulching, crop rotation, tilling practices and the like can be made from the derived map and field profile.

An object of the invention is to provide an apparatus and method that will provide real-time soil compaction profiles for an entire field.

Another object of the invention is to provide a soil profile monitoring device that is accurate, easy to use, provides a visual display of obtained profile data that is easy to understand and is relatively inexpensive to manufacture.

Another object of the invention is to provide a soil compaction map with respect to soil depth and field position.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings that are for illustrative purposes only.

DETAILED DESCRIPTION OF THE INVENTION

Figure 1:
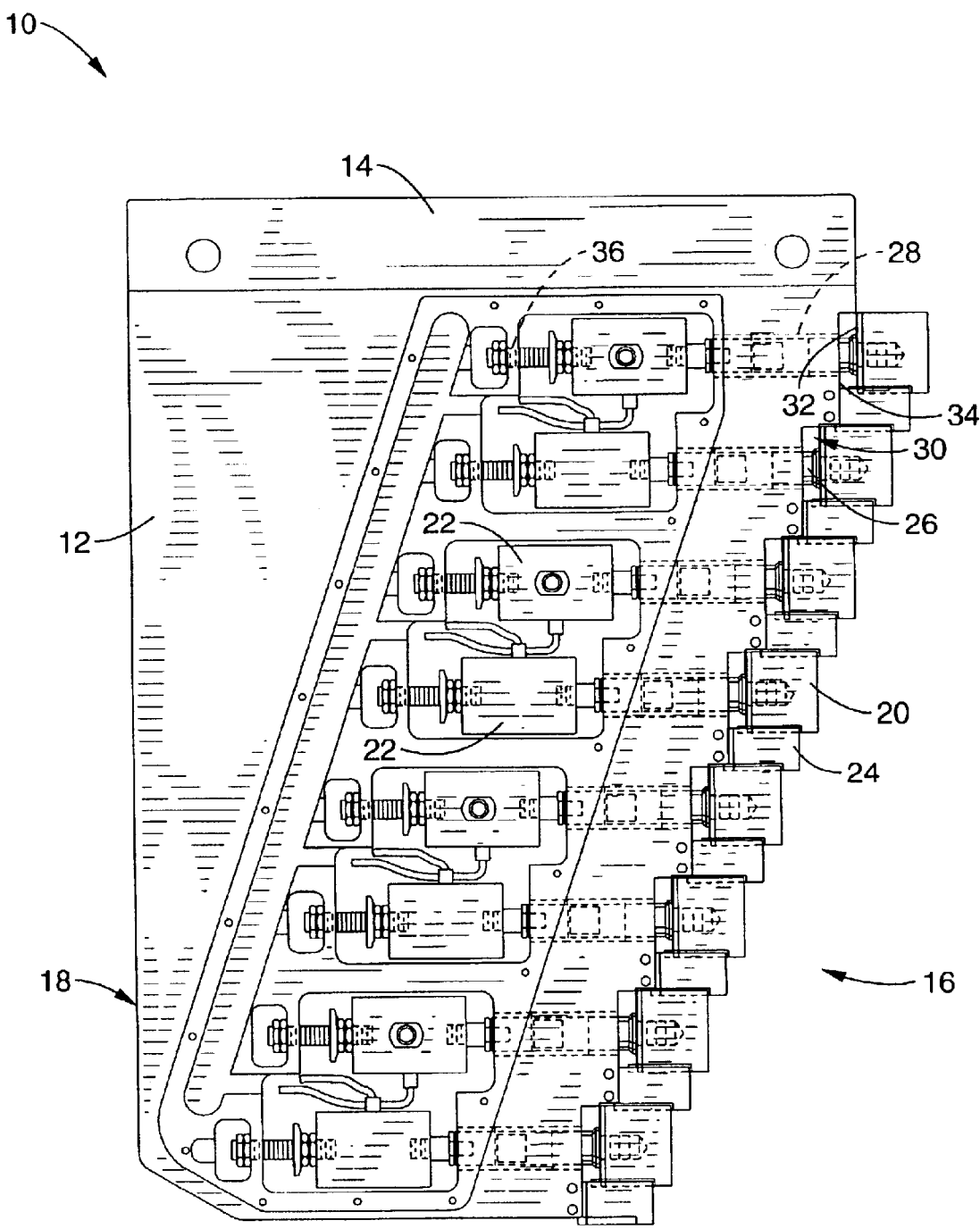
FIG. 1 is a side view of a profile sensor apparatus according to the invention configured to be mounted on a farm tractor.
Figure 2:
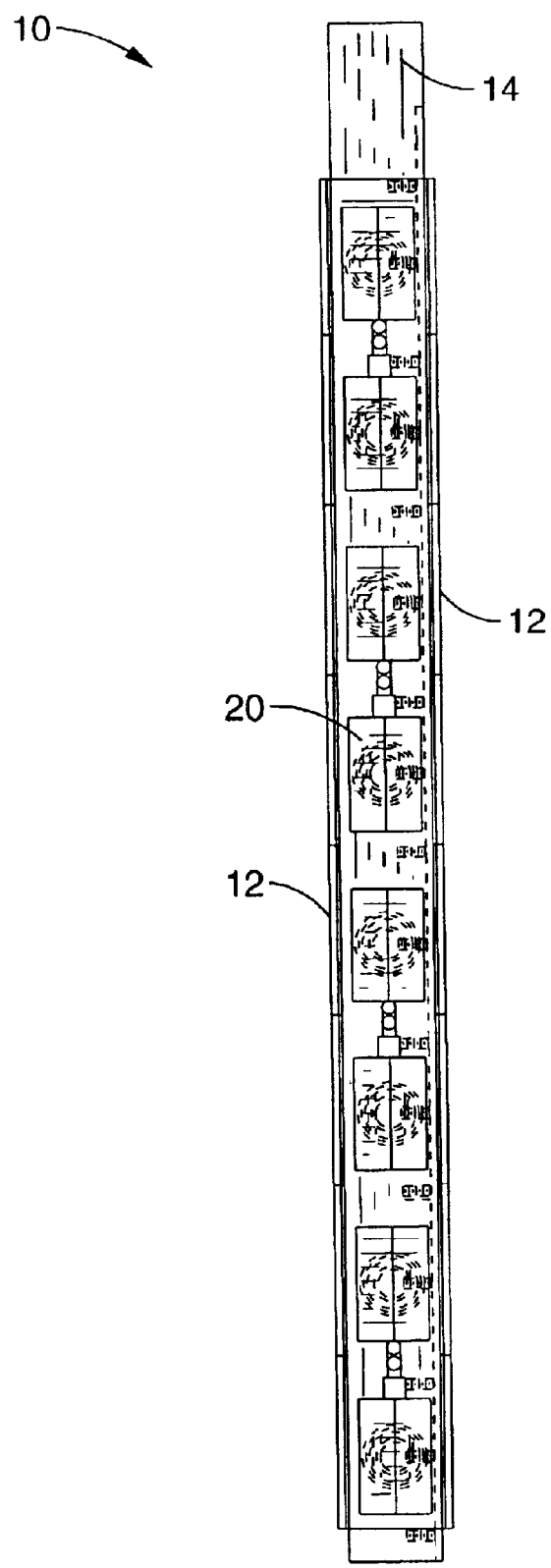
FIG. 2 is a front view of the apparatus shown in FIG. 1 with the dummy cutting elements removed for clarity.
Figure 3:
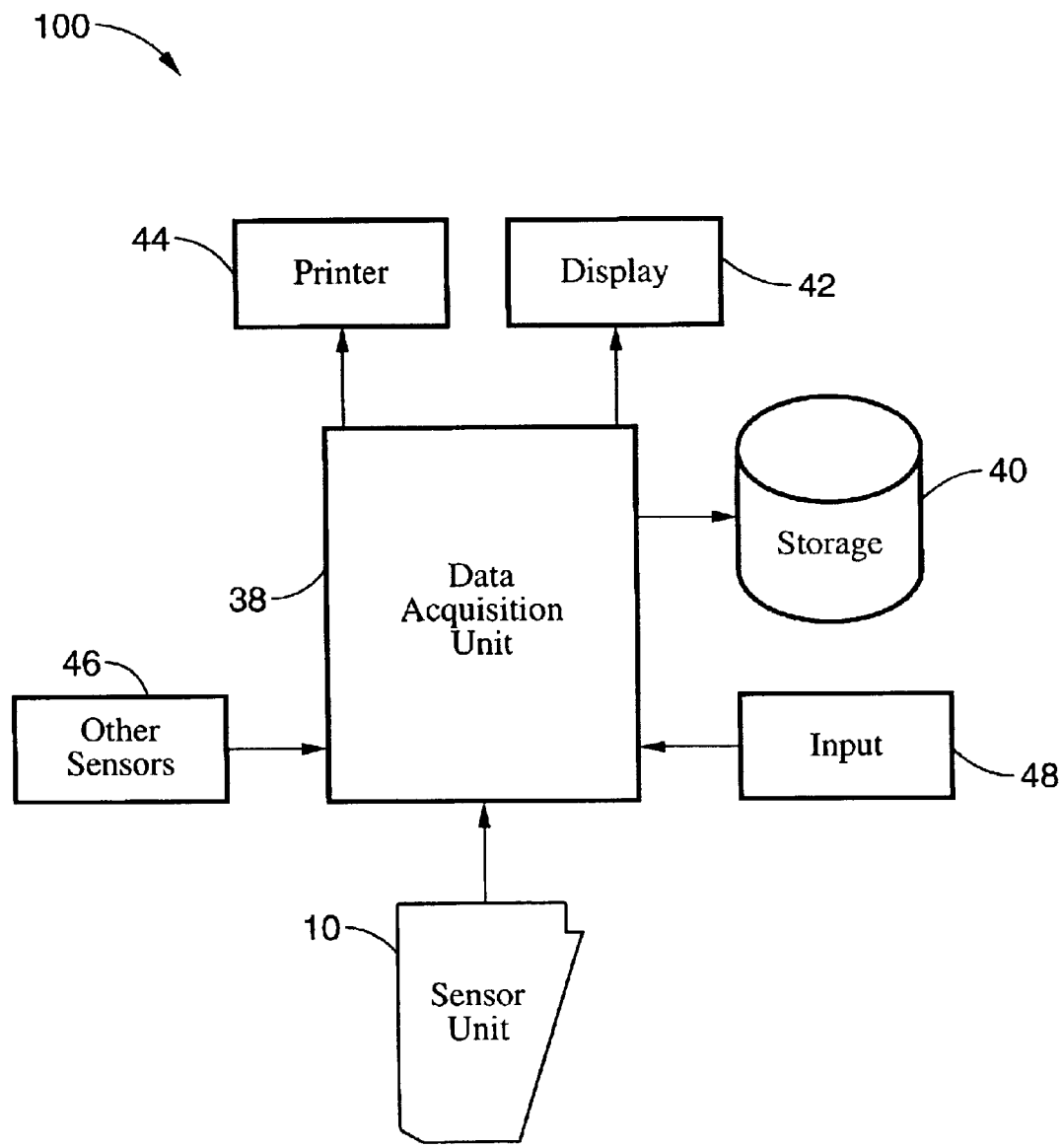
FIG. 3 is a schematic diagram of one embodiment of a profile sensor apparatus system according to the present invention.

Referring first to FIG. 1, FIG. 2 and FIG. 3, an embodiment of a profile sensing tine apparatus 10 in accordance with the present invention is generally shown. In the embodiment shown, the apparatus 10 includes a tine body 12 (e.g., thick metal plate similar to a conventional tine) that is configured to be mounted vertically to a tractor or a trailer or other towed apparatus. However, unlike a conventional tine which has a cutting edge, in the present invention a plurality of cutting elements are coupled to the tine body through a plurality of corresponding load sensing elements as described in more detail below. In use, the tine body preferably would be pivotally mounted to the tractor or towed apparatus with a bracket 14 and configured to be raised and lowered into the soil during use by hydraulic or pneumatic systems known in the art. The tine body therefore serves as a platform for the placement of load sensors and associated cutting elements to be drawn through the soil profile at incremental depths.

In the embodiment shown in FIGS. 1 and 2, the apparatus has a leading edge 16 and a trailing edge 18. A plurality of independent cutting elements 20. such as metal blades or the like, are positioned along the tine body to form the leading edge 16 which Is the active cutting edge. Each cutting element is supported by an independent load sensing element 22, preferably a conventional load cell, and each load sensing element 22 is in turn attached to the tine body 12. In this way, the load sensing elements 22 will measure the force exerted on the cutting elements 20 as the active cutting edge of the tine assembly is pulled through the soil.

In FIG. 1 and FIG. 2 a total of eight cutting elements 20 and associated load sensing elements are shown as an example, but the actual number used typically will be based on the physical size and cutting area of the tine. Each cutting element 20 preferably provides cutting resistance over a 5-cm layer in this embodiment. The edge shape of the cutting elements 20 may be virtually any angular shape but is preferably the commonly used wedge shape found in a conventional tine.

In the embodiment shown, the apparatus is capable of providing information on soil resistance to cutting for every 7.5-cm layer (5 cm of this 7.5 cm comprises an active cutting element 20 and the other 2.5 cm comprises a dummy element 24) up to a total depth of approximately 60 cm. Dummy elements 24 separate the cutting elements 20 along the leading edge 16 of the assembly and thereby reduce interference between different active cutting elements 20.

Each active cutting element 20 is preferably coupled to a corresponding load sensing element 22 by a threaded shaft 26 that is disposed in a channel 28 in tine body of tine 12. Preferably there is a gap 30 of approximately 0.015 inches between the distal edge 32 of the cutting element and the proximal edge 34 of tine body 12. When a cutting element 20 is subjected to a cutting force during field operations, the cutting force is transferred to the corresponding load sensing element 22 via shaft 26 and recorded by a data logger or other recording device. Note that it is important to keep this 0.015 inch gap free from sand, soil particles or other debris in order for the apparatus to function properly since a buildup of foreign particles will prevent movement of cutting element 20. This is preferably accomplished by filling or sealing the gap 30 with an RTV compound or like material.

Preferably the apparatus incorporates an overload safety protection system to protect the load sensing elements 22 from excessive load forces during use. It is preferred that cutting load forces in excess of approximately 2500 foot pounds activate the overload safety system. In the embodiment shown in FIG. 1 and FIG. 2, the overload safety protection system comprises a spring washer 36 located at the point where a load sensing element 22 is coupled to tine body 12. The maximum allowable deformation for a load sensing element 22 is preferably approximately 0.005 inches at rated load. The spring washers 32 are so designed that they will deform approximately 0.010 inches when load sensing elements 22 experience the rated load. Preferably, the total deformation at rated load is approximately 0.015 inches, which deformation causes the active cutting element 20 to contact the proximal edge 34 of tine body 12. When this occurs, any additional force on the active element will be transferred directly to the body of the tine, which protects the load sensing element 22 from overload. Prior to testing the subject field, each load sensing element, which is connected to its corresponding active cutting element 20, is preferably calibrated with the aid of a Tinius Olsen loading machine or similar device.

While eight active cutting elements 20 and associated load sensing elements 22 are preferred, it will be understood that any number of cutting elements and force measuring devices may be used to provide force measurements without departing from the scope of the present invention. Additionally, although a single tine with a number of cutting elements is preferred, it will be understood that any number of tines with resistance sensors positioned at varying depths can be used in the alternative to the single tine shown in FIG. 1 and FIG. 2.

In use, the apparatus is drawn through the soil at a preferred constant speed of between approximately 0.65 meters per second and approximately 1.25 meters per second. While this range of speeds is preferred, it will be understood that the apparatus will function at operating speeds outside of this range of speeds. Tests reveal that there are no statistical differences in the disclosed methods between soil cutting forces at normal field speeds.

It will be seen that this invention provides an apparatus and method for analyzing soil compaction and other soil characteristics using force measurements and producing positional readings at incremental depths in the soil profile that allow field maps to be created. Referring now to FIG. 3, one system 100 using the instrumented tine 10 of the invention is schematically shown. In this embodiment, the measurements produced from the load sensing elements 22 are preferably received by a data acquisition unit 38. The force measurements and other sensor data are preferably monitored and recorded in real-time by the data acquisition unit 38 and storage device 40, respectively, that are configured to take readings at variable time points. In one embodiment, the data is logged in a data logger configured to store the data in a magnetic or electronic storage device 40. In this embodiment, the data is taken from the storage device 40 and interpreted and printed away from the field.

In another embodiment, the data acquisition unit 38 is a computer. Software programming can be used to compute and graphically display the readings from load sensing elements 22. For example, the software can compare the current readings with prior readings within the same fields and locate areas of statistical differences for display in a three-dimensional display 42. Alternatively, the data can be presented in textual form on display 42.

The data acquisition unit 38 may additionally have a monitor, plotter or printer 44 to display the acquired and computed data in graphical or textual form. For example the monitor may display a bar graph of each measurement over time.

In one embodiment, the data acquisition unit 38 is operably coupled to other sensors 46 located on a vehicle or implement platform or the tine assembly itself. Such sensors 46 may include position sensors including sub-meter GPS sensors as well as temperature sensors, alkalinity sensors, speed sensors such as radar and moisture sensors and the like. Measurements from these sensors 46 are also acquired by the data acquisition unit 38 and preferably recorded and displayed by display 42 in real-time or logged for further analysis away from the field. Preferably, the sensor measurements are correlated with the field position points from the GPS or determined mathematically with speed and time. Sensor readings will have a field position component in this embodiment.

In another embodiment, the data acquisition unit 38 is configured to receive historical and other data input 48 to be compared with the sensor data. For example, field data from other sources such as satellite images, chlorophyll meter readings, nitrogen content data, soil moisture meter readings, penetrometer data, historical sensor data or global positioning system data and the like can be entered into the computer to be correlated and compared with the data received from the sensors.

Furthermore, a history of measurements and data for a particular field may be maintained and compared to disclose trends. Accordingly, the field sensor data can be evaluated and agricultural decisions made concerning the needed field activities with all available data.

Alternatively, the data can be logged and interpreted away from the field and preferably mapped. Such maps and data may be compared with previous maps and data for the same field as well as with satellite soil survey maps and the like.

Thus, soil compaction data for a particular field can be monitored in a variety of ways and a history of the field can be compiled. For example, differences soil compaction level evaluated and compared with other readings during different stages of the growing season for a particular crop as well as from season to season. The effectiveness of changes in tillage and irrigation practices or increases or decreases in organic matter percentages, and the like can be evaluated and optimized. Intra-seasonal and inter-seasonal trends relating to compaction, and other sensor data can be observed. It can be seen that the readings and maps produced by the instant invention can be useful with other precision farming techniques. For example, this sensor can be used to detect the presence of hard layers within the soil throughout the field. Tillage frequency and depths can be adjusted on a site-specific basis leading to prescription tillage. Prescription tillage can reduce tillage energy requirements and reduce soil erosion potential.

The apparatus of the present invention has the potential to play a critical role in optimizing overall performance of a tractor by continuously adjusting its gear ratio and draft requirements of the tillage tools such that tractive performance (high output draft energy for low input axle torque energy) is maximized while engine fuel consumption is minimized. In operation, the torque output of the engine, ground speed of the tractor, and compaction sensor output would be monitored. Based on the compaction sensor readings and the engine operating characteristics, the proper gear ratio would be selected and implement depth or tractor forward speed controlled to maximize output draft power while minimizing engine fuel consumption. Therefore, system efficiency can be maximized by monitoring engine torque, measuring the draft requirements of the tillage tools and manipulating the engine efficiency. The method may be particularly effective with tractor designs that have infinitely variable transmissions.

It has been shown that the soil cutting force is influenced by the soil compaction level, moisture content of the soil and the depth of operation of the tine in the soil profile. The lack of soil moisture due to poor soil infiltration characteristics, which is associated with increased levels of soil compaction and/or soil texture, is one of the primary reasons for reductions in crop yield.

Knowledge of the physical properties of the soil that are associated with the moisture status of the soil is important for efficient irrigation use, tillage and fertilizer application practices and may be manipulated to increase crop production. Likewise, possible long-term effects of soil compaction may be avoided through tillage and other techniques if soil compaction can be quantified and monitored. However, current methods of measuring soil compaction and texture are tedious, time consuming, and expensive.

One approach frequently taken to investigate the variability in physical properties of the soil is the measurement of soil strength indices such as the Cone Index. A cone index for a soil indicates the soils resistance to a quasi-static vertical penetration. The Cone Index (CI) is determined by measuring the penetration resistance of soils by measuring the force required to push a 30° circular cone through the soil at a constant rate. Since the cone penetrometer interacts with the soil on a local level, it provides measurements that may characterize the soil in only a small region around the penetration test. Because the Cone Index is a point measurement it is also subject to great variability between measurements. Accordingly, ASAE standard S312.2 sets a minimum of five observations to be averaged in order to represent the cone index at a specific point.

In contrast, Texture/Compaction Index (TCI) sensor monitors soil cutting force continuously over the entire tillage depth that provides a single measure of average soil compaction over the whole profile.

Soil cutting force measurements provide meaningful data that can be used for the assessment of the physical state of the soil. In general, these types of measurements depend on multiple soil properties (e.g. bulk density, moisture content, texture) and thus provide a composite soil parameter that does not represent any single soil property. These composite soil parameters often correlate with other soil parameters such as infiltration characteristics, which in turn depend on similar soil properties. Since variability in infiltration characteristics and hydraulic conductivity are related to the variability in soil compaction or bulk density with respect to depth, it is desirable to map the variability in soil compaction with respect to depth. However, the Texture/Soil compaction Index unit provides only a single measurement for a given site and does not provide variability in soil compaction level with depth. The current invention uses a series of load sensing devices to sense the soil compaction profile.

The cutting resistance of soil, $F_i$, at a given depth and forward speed is expected to be a function of:

$$F_i = f_i(\rho_i, \theta_i, \zeta)$$

where:
$F_i$=force requirements of layer i (kg);
$\rho_i$=bulk density layer i (g/cm$^3$);
$\theta_i$=moisture content of layer i (% on volume basis); and
$f_i$=function operator determined through calibration.

In order to analyze the results, a modified version of equation is preferably used assisted by using dimensional analysis as follows:

$$F_{i,j} = f(d_i, D_j, w, \theta_i, \rho_i, g, v, \zeta)$$

where:
$F_{i,j}$=force measured by the cutting element at depth $d_i$ when operating at depth
$D_j$ (kN); $d_i$=depth of the $i^{th}$ layer (i.e., location of cutting element with respect to surface) (m); $D_j = j^{th}$ depth of operation (m);
w=width of cutting element (0.051 m);
$\theta_i$=moisture content of layer i (% m$^3$/m$^3$);
$\rho_i$=bulk density of layer i (kg/m$^3$×1000);
g=gravitational acceleration constant (9.81 m/s$^2$);
v=ground speed; and
$\zeta$=soil texture.

Note that if the ground speed is held constant and the soil texture is the same within the test plots, both the velocity v and soil texture $\zeta$ variables can be eliminated. Using dimensional analysis, the equation can be rewritten in the following form:

$$\frac{F_{i,j}}{\rho_i g w^3} = Y = f\left(\frac{D_j}{w}, \frac{d_i}{w}, \theta_i\right).$$

To minimize multicolinearity problems and to enhance stability of regressional analysis the independent variables are preferably normalized as follows:

$$\frac{d_i^*}{w} = \frac{\frac{d_i}{w} - \frac{\bar{d}}{w}}{\frac{\left(\frac{d}{w}\right)_{max} - \left(\frac{d}{w}\right)_{min}}{2}}.$$

The present invention may be more particularly described in the following examples that are intended for illustrative purposes only, since numerous modifications, adaptations and variations will be apparent to those skilled in the art.

EXAMPLE 1

A preliminary analysis of the data using regressional analysis showed non-constancy of error terms. In particular error terms tended to grow as the cutting force increased. This problem was solved by transformation of the dependent variable as follows:

$$Y^* = \sqrt{Y}.$$

The stepwise regressional analysis of the transformed data using linear and quadratic terms involving (d/w), D/w, and θ resulted in the following model:

$$Y^* = a_1\theta_i + a_2\theta_i^2 + a_3(d_i/w) + a_4(D_j/w) + a_{1,3}\theta_i(d_i/w)^* + a_{1,4}\theta_i(D_j/w) + a_{3,4}(d_i/w)(D_j/w)^*$$

where:

a$_1$=0.879;

a$_2$=−0.015;

a$_3$=4.633;

a$_4$=3.247;

a$_{1,3}$=−0.241;

a$_{1,4}$=−0.059; and a$_{3,4}$=2.233.

The resulting model has a coefficient of multiple determination, $r^2$ value of 0.978, indicating an excellent empirical model for the profile cutting force. Additionally, the output of the profile sensor should be well correlated with the soil cone index values. The relationship between the profile sensor output and soil cone index values were found to be:

$$F_i = a_0 + a_1 d_1 + a_2 CI_i + a_3 CI_{i-1}$$

where:

$CI_i$=cone index of soil in front of the $i^{th}$ load cell;

$CI_{i-1}$=cone index of the soil layer immediately above the $i^{th}$ load cell;

a$_0$=−242.915;

a$_1$=49.368;

a$_2$=0.306; and a$_3$=0.496

Accordingly, it can be seen that there is a relationship between the cutting force exerted on the tine as it is drawn through soil and the moisture content of the soil as well as the soil compaction or bulk density of the soil at various depths in the soil profile.

EXAMPLE 2

Figure 4:
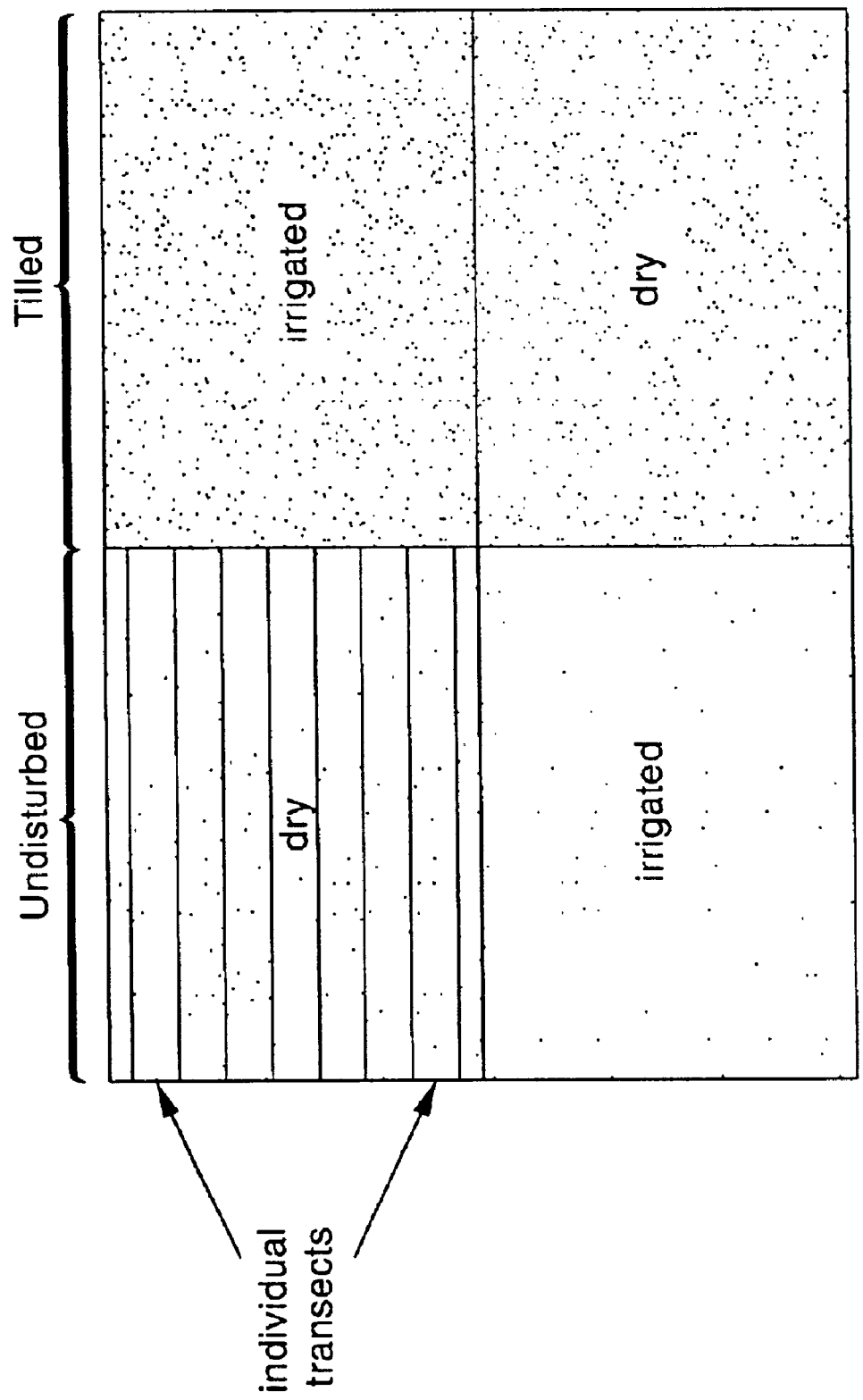
FIG. 4 is a schematic diagram of a typical field block of an experimental design according to the present invention.

To test the performance of the profile sensor tine under different conditions a very extensive field test that included four different soil conditions using a loam type of soil of the Yolo series was conducted. Referring to FIG. 4, the test plot with tilled and undisturbed sections and irrigated and dry sections is shown. The tilled sections consisted of ripping the soil to 60 cm depth and subsequent discing of the top 15 cm of the section. The undisturbed sections consisted of land left fallow during the previous fall and winter seasons. The tilled and undisturbed sections were randomly bifurcated into sub-plots that were either irrigated or left dry. The irrigated sub-plots were exposed to 30 hours of sprinkler irrigation until the soil was saturated to a depth of 40 cm.

Finally, transect runs were performed in each of the sub-plots. Each transect run had a length of 75 m, and there were 1.5 m of separation between each run. The average velocity of operation of the tine was 0.63 m/s.

Transect runs were conducted at eight equally spaced depths ranging from 7.6 cm to 61 cm from the surface. The experimental design accommodated four replicates producing a total of 128 individual transect runs. These runs were also randomly allocated within each plot.

At the time of field tests, Cone Index measurements were obtained using a standard tractor-mounted, hydraulically driven, self-recording cone penetrometer that was able to reach an operating depth of 53 cm for comparison. Additionally, with the use of a neutron probe strata-gauge, soil moisture content and density profiles from 5 cm to 61 cm were recorded with a resolution of one value for each 5 cm depth. The data acquisition system of the profile sensor tine was set to record the output of all eight load cells and one ultrasonic distance (depth) sensor simultaneously at a sampling frequency of 2 Hz. The results were analyzed statistically through the use of ANOVA and Multiple Linear Regression techniques.

For purposes of comparison, the moisture content and bulk density of the soil in the various sub-plots at the time of the tests were determined at depths up to 60 cm. It is usually difficult to create different soil conditions at the field level through soil manipulation such as tillage for testing purposes. It becomes even more difficult if such soil conditions have to be attained to a depth of 60 cm. It was observed that there was a lack of differentiation between soil conditions with respect to bulk density although there was a substantial energy input during tillage. Statistical analysis revealed that tillage did not affect the bulk density status of the soil significantly. Analysis of Variance (ANOVA) showed that tillage affected soil-cutting force the least, especially at deeper depths of operation. On the other hand, moisture status data suggests that this parameter was controlled quite successfully up to a depth of 40 cm. ANOVA results indicate that the effect of irrigation on force measurements was always significant. This effect was highly pronounced at shallower depths.

Average values of Cone Index and profile forces at an operational depth of 53 cm were obtained for analysis. These indices provide very different profiles primarily because they measure different aspects of the mechanical state of soil strength. Cone Index values are strongly associated with the moisture regime of the soil but its profile distribution has significant similarity with the profile distribution of bulk density. The nature of the correlation between Cone Index and soil parameters such as bulk density and moisture content might reside in the direction of the measurement. Cone Index measures the soil reaction in the vertical direction that coincides with the gradient of those two parameters. In the case of the profile sensor tine of the present invention, soil is cut in the horizontal direction and the distribution of forces has a distinctive shape that does not appear to be similar to either bulk density or soil moisture profile. This outcome is most likely related to the effect of anisotropy in soil strength properties on soil failure mechanism.

Figure 5:
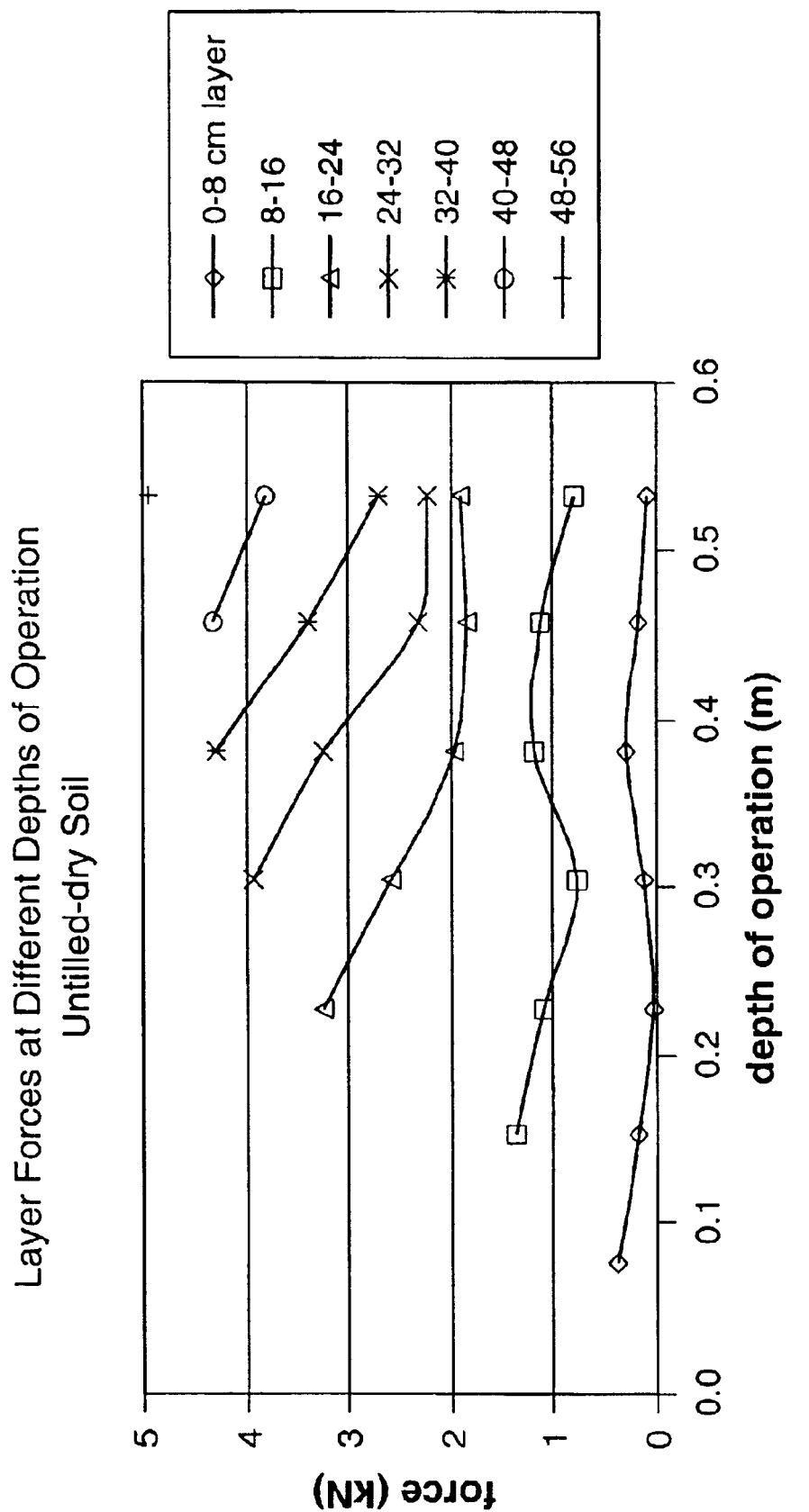
FIG. 5 is a graph showing typical cutting force requirements in an untilled dry soil condition in Yolo loam soil.

After ANOVA tests were completed, a series of multiple linear regression tests to develop meaningful relationships between soil cutting force and soil physical properties were performed. Since the profile sensor releases information on a stratified basis, it is important to analyze the effect of depth on force readings as two variables rather than just one. One variable is the location of each of the active cutting elements with respect to the surface (d); the other refers to the total depth of operation (D). The conception of depth in two different forms is clearly justified by a visual inspection of FIG. 5 where the dependence of cutting force on both the depth of operation and the location of the cutting element is evident. This trend was found to be consistent across soil conditions.

Figure 6:
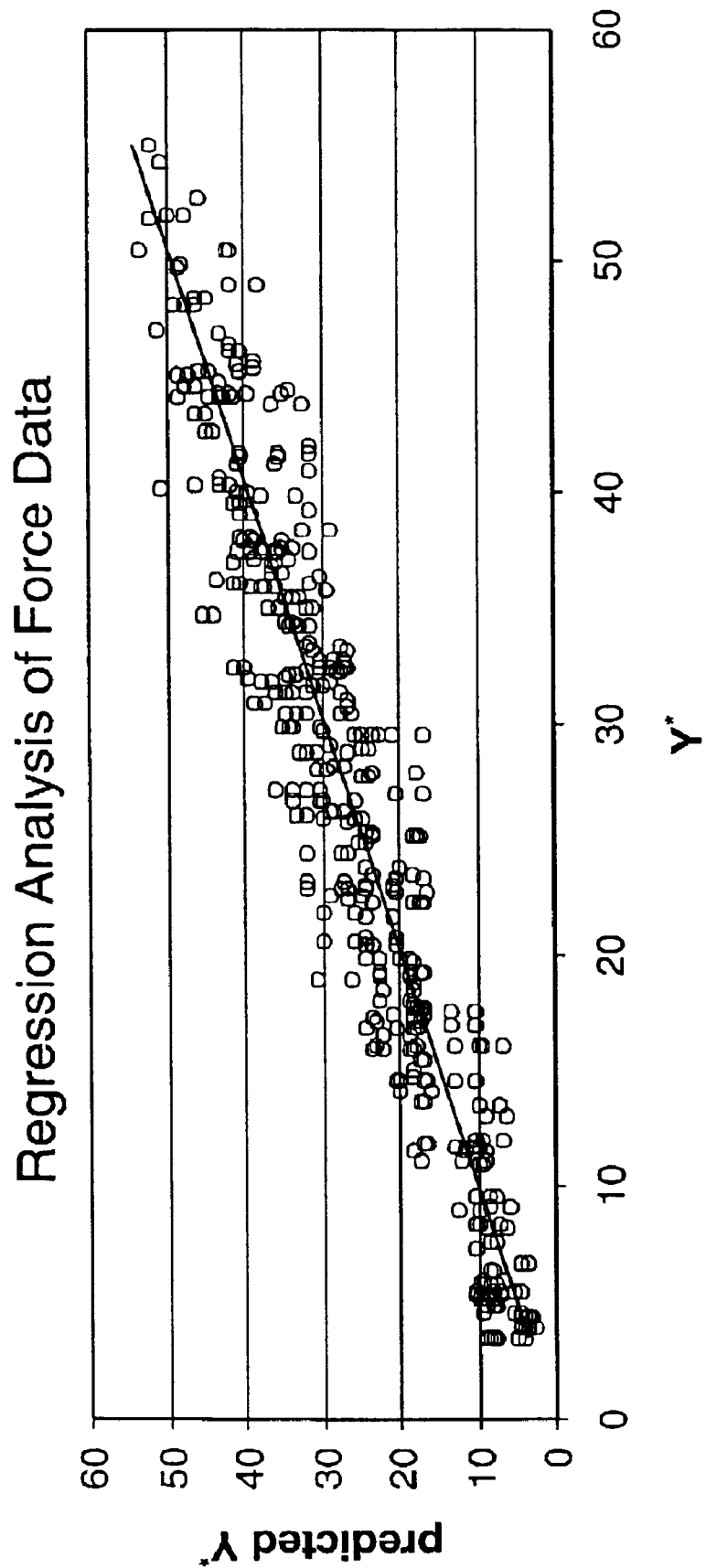
FIG. 6 is a plot of a regression analysis for cutting force through Yolo loam soil.

Turning now to FIG. 6, a regression analysis of the obtained force data with the predicted using the disclosed model indicates that the model of has an exceptionally high coefficient of multiple determination ($r^2$=0.978). Accordingly, the model using cutting force data is considered an accurate model.

EXAMPLE 3

The profile sensor of the present invention was tested using a plot of a clayey soil of the Capay series and a plot of sandy soil of the Metz series. Each plot was divided into three sub-plots where the main differentiating factor was moisture status. The first sub-plot was at field capacity. The second sub-plot was at medium moisture. The third sub-plot was dry ground. Each sub-plot was 60 meters in length and 8 meters in width. Two linear transects of each sub-plot were conducted at speeds of operation of 0.65 meters per second and 1.25 meters per second and 4 meters apart. The depth of operation was kept constant at 45 cm from the surface.

The data acquisition system in the profile sensor tine was set to simultaneously record information on forces, as well as depth and speed of operation at a sampling frequency of 10 Hz.

The physical state of the soil was determined at the time of the tests for comparison by measuring the volumetric moisture content and dry density profiles using a neutron probe strata-gauge. The probes of this device penetrated into the soil profile up to a 45 cm depth and were capable of providing information with a resolution of one value for every 5 cm depth. In addition, cone index measurements from the top surface up to a depth of 50 cm were taken at discrete intervals of 6 mm. using a standard tractor-mounted, hydraulically driven, self-recording cone penetrometer.

It was observed at the time of the field tests that the moisture content increased with depth and saturated at a high value in both sandy and clayey fields. Predictably, dry soil conditions had lower moisture content values throughout the soil profile in both soils. In the sandy soil, the dry density values increased with depth and reached peak values at about 20 cm to 22 cm and then tended to decrease. This indicated the presence of a hardpan at about 20 cm to 22 cm depth. In the clayey soil, on the other hand, the density values increased with depth up to 20 cm and then leveled off, which indicates that well developed hardpan does not exist in this plot.

Statistical software SAS v. 8.3 and Statview v. 4.5 were used for all statistical analyses. Analysis of variance (ANOVA) was used to test the null hypothesis that the two speeds of operation had no statistically significant effect on the output of the apparatus. There were no statistical differences between soil cutting forces at low (0.65 m/s) and high speed (1.25 m/s) in the entire 45 cm soil profile in both soils and at any of the three soil moisture contents that were tested.

A stepwise regression procedure was used to relate the profile sensor output to soil physical properties as suggested by the model.

Figure 7:
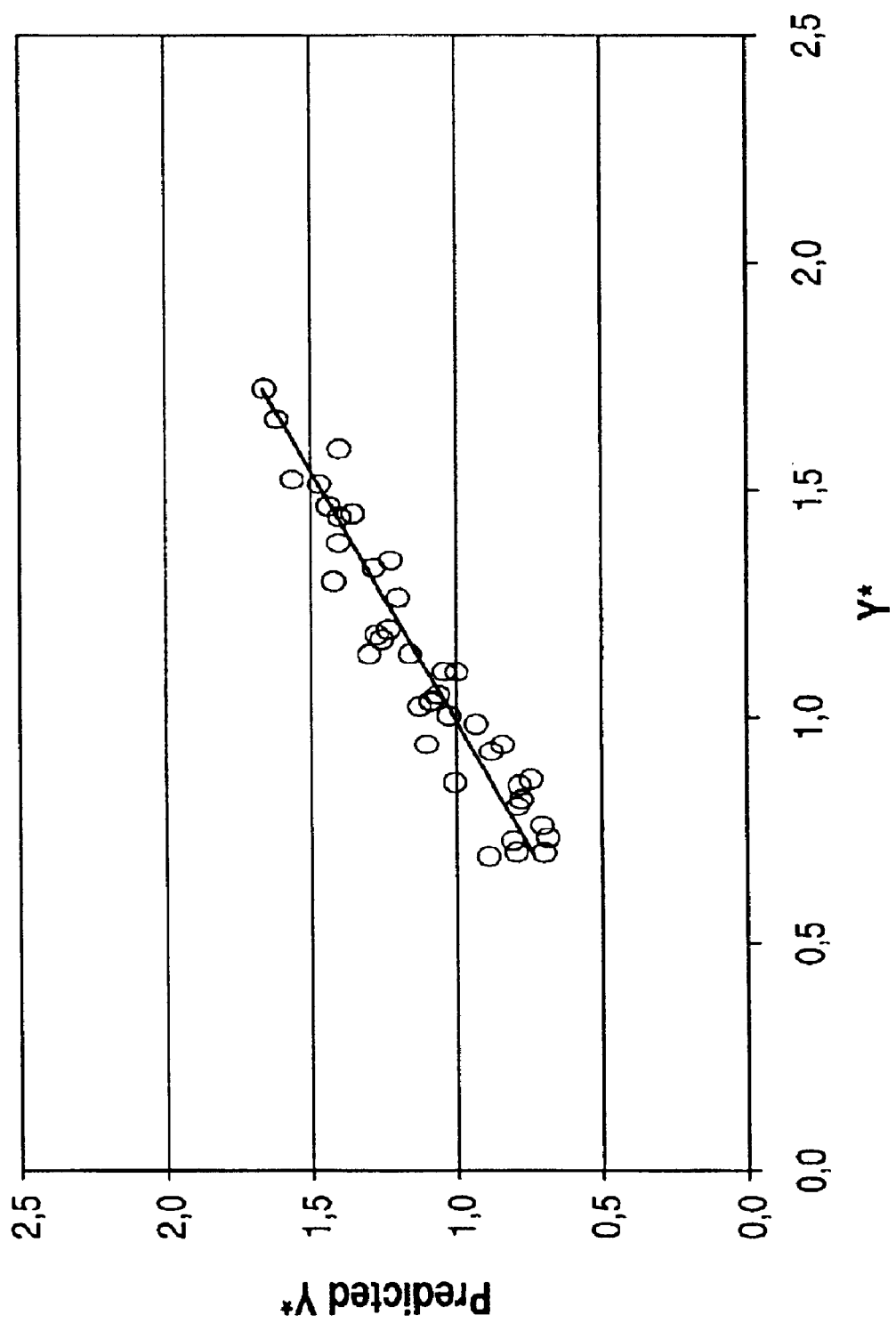
FIG. 7 is a plot of a regression analysis for soil cutting force through a 45-centimeter soil profile in a Yolo loam field with a tine according to the present invention.
Figure 8:
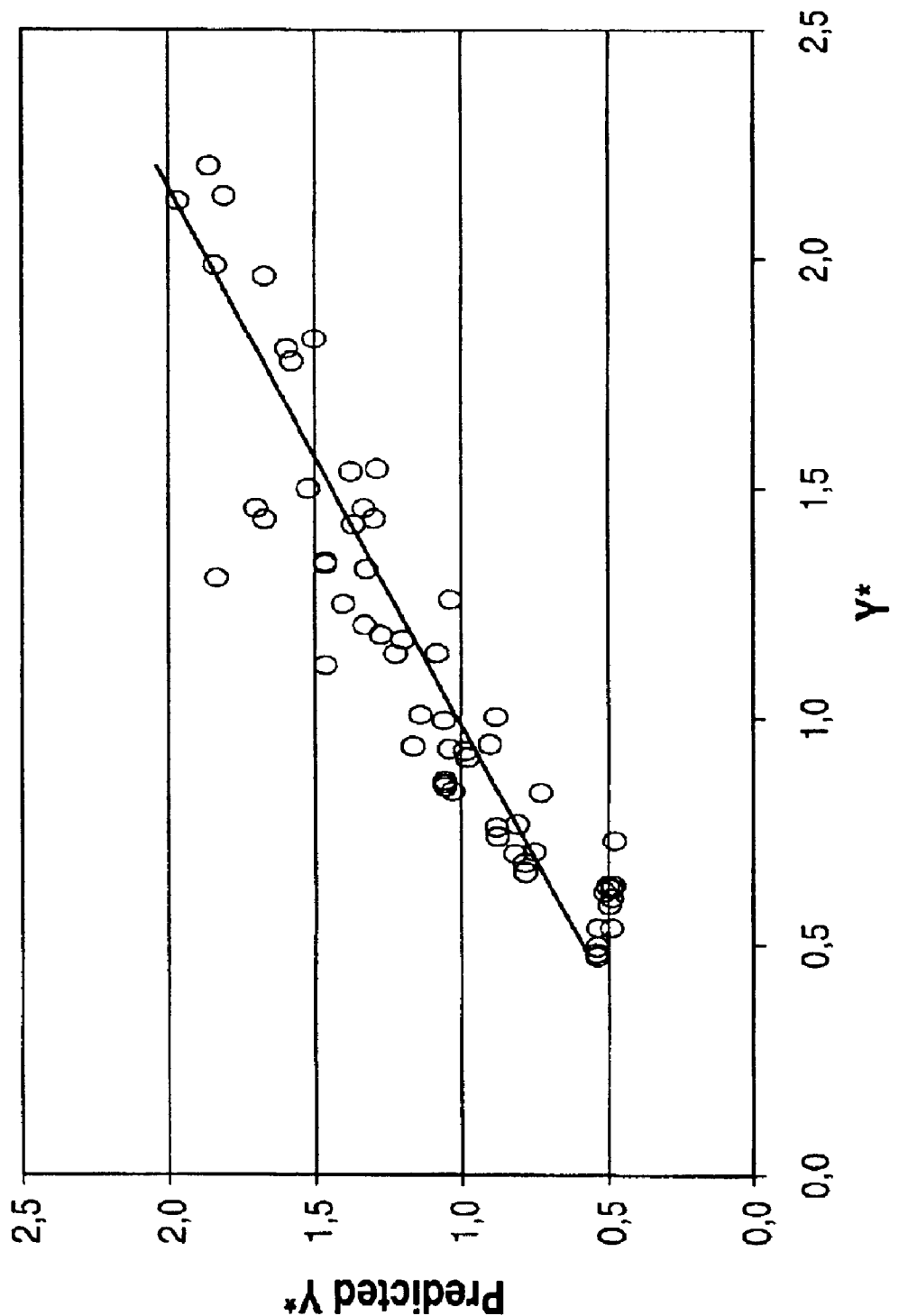
FIG. 8 is a plot of a regression analysis for soil cutting force through a 45-centimeter soil profile in a Capay clay field with a tine according to the present invention.
Figure 9:
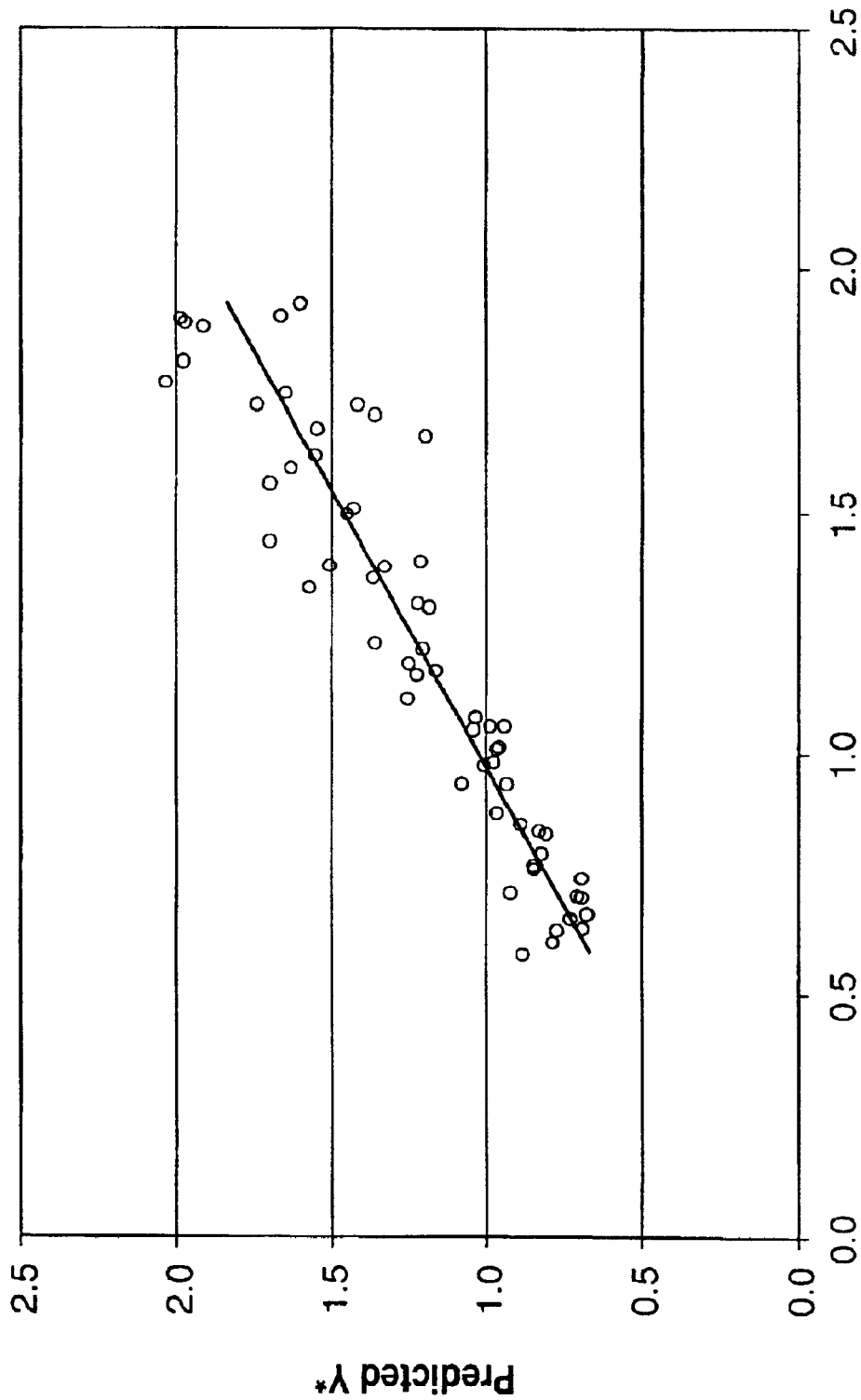
FIG. 9 is a plot of a regression analysis for soil cutting force through a 45-centimeter soil profile in a Metz sand field with a tine according to the present invention.

Turning now to FIG. 7, FIG. 8 and FIG. 9, the predicted versus actual values of nondimensional soil cutting force within a 45 cm soil profile for a Capay clay field and a Metz sand field are shown in FIG. 8 and FIG. 9 respectively. These results were compared with the results of the tests if the Yolo loam converted from Example 1 and shown in FIG. 7. The prediction equation used to produce FIG. 7, FIG. 8 and FIG. 9 is as follows:

$$Y^* = a_0 + a_1\theta + a_2(d/w^*) + a_3\theta(d/w^*)$$

where for the Yolo loam field:
$a_0$=1.527;
$a_1$=−0.018;
$a_2$=1.142;
$a_3$=−0.020; and
$r^2$=0.905.
For the Capay Clay field:
$a_0$=1.666;
$a_1$=0.02;
$a_2$=1.821;
$a_3$=−0.027; and
$r^2$=0.853.
For the Metz Sand field:
$a_0$=1.71;
$a_1$=−0.029;
$a_2$=1.088;
$a_3$=−0.14;
$r^2$=0.872;

Although the actual values of the regression coefficients are slightly different between the three equations, the equations contain similar variables and have very high coefficients of multiple determination.

Figure 10:
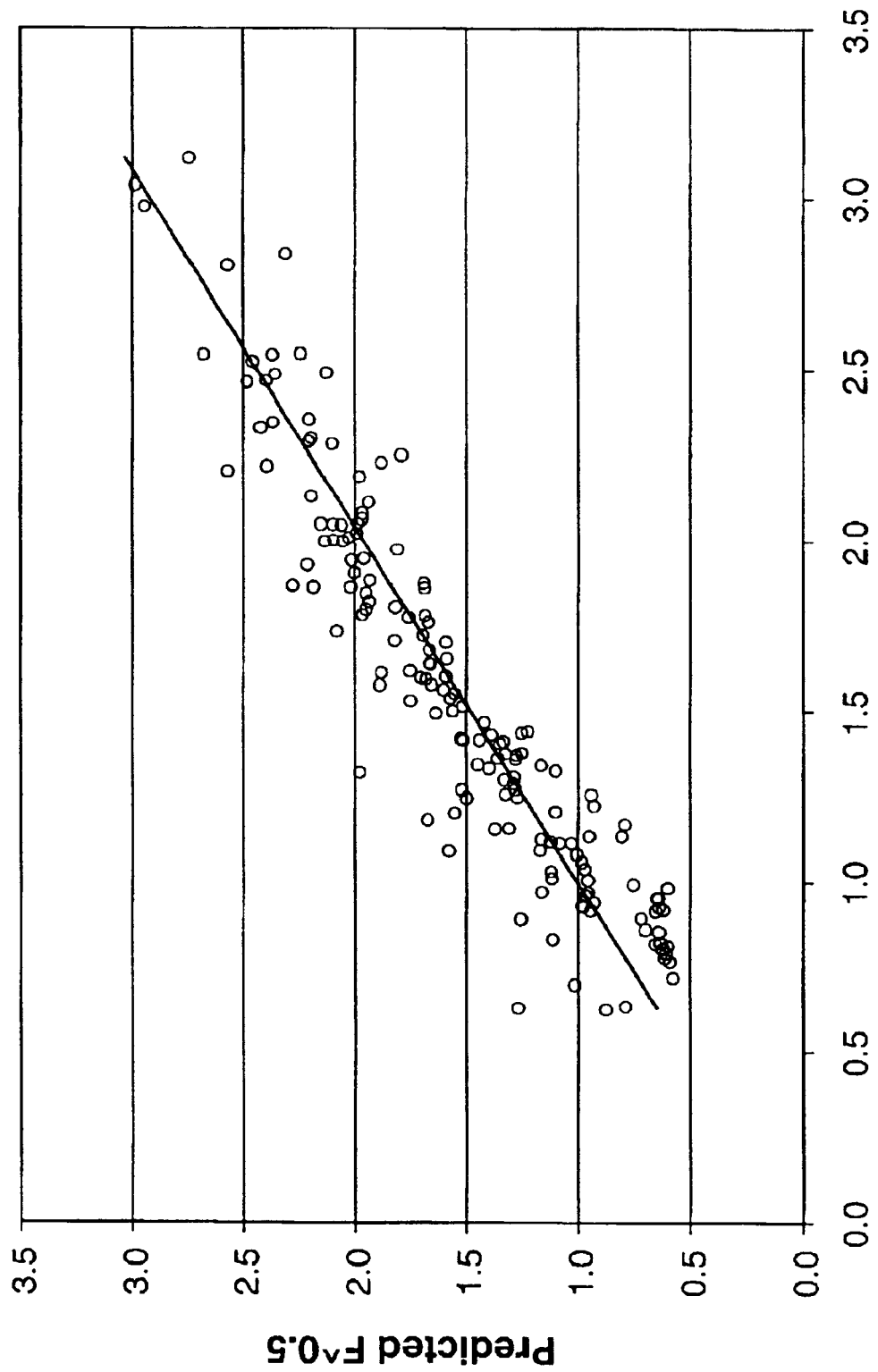
FIG. 10 is a plot of predicted verses measured soil compaction profile sensor output based on Cone Index values measured using a standard cone penetrometer.

Turning now to FIG. 10, a plot of predicted versus measured soil compaction profile sensor output based on Cone Index values measured using a standard cone penetrometer is shown. FIG. 10 shows the relationship between predicted and measured soil profile sensor output values for all three soil types and different soil conditions (i.e. different soil moisture content levels) included in this study. The relationship between soil profile sensor output and Cone Index values is given by the following equation:

$$Y^* = a_1 CI + a_2 d + a_3 CI(d)$$

where:
$a$=1.603E-4;
$a_2$=0.038;

$a_3=2.74E-6$; and
$r^2=0.985$.

It can be seen that there is a very high coefficient of multiple determination, $r^2$ value, of 0.985 indicating that the profile sensor output correlates well with soil Cone Index values.

Accordingly, the output of the soil compaction profile sensor depended on the location of the sensing element within the soil profile, soil moisture content, and bulk density in clayey, loamy, and sandy soil conditions. The stepwise regression analysis indicated that the profile sensor force prediction equations had very high coefficients of multiple determination, $r^2$ values, for all three soil types. Furthermore, the operating speed of the soil compaction profile sensor did not significantly influence the soil cutting force profile in sandy as well as clayey soils at any one of the three soil moisture contents tested.

Thus, it can be seen that the present invention provides an apparatus and method for quantifying soil compaction throughout a field of any type of soil using a tine or tines to provide soil cutting data. The tine and support apparatus may also carry other sensors that can provide coordinated data with the cutting data. For example, depth sensors, moisture sensors and field position sensors, known in the art, can also be used to provide additional data for correlation.

Although the description above contains many specificities, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A compaction profile sensing tine apparatus, comprising:
   (a) a plurality of cutting elements;
   (b) means for measuring force on each of the cutting elements as said cutting elements are pulled through soil, wherein said means for measuring force on the cutting elements comprises:
      (i) a plurality of independent load sensing elements;
      (ii) each said load sensing element coupled to a corresponding cutting element;
      (iii) each said load sensing element configured for measuring force on a corresponding cutting element as said cutting element is pulled through soil;
   (c) a tine body;
   (d) wherein said plurality of load sensing elements are coupled to said tine body.

2. An apparatus as recited in claim 1, wherein said plurality of cutting elements form a cutting edge of a tine.

3. A compaction profile sensing tine apparatus, comprising:
   a plurality of cutting elements configured to form the cutting edge of a tine;
   means for measuring force on each of the cutting elements as said cutting elements are pulled through soil;
   means of measuring soil temperature and/or soil cutting speed;
   a data logger coupled to said force measuring means along with said temperature and/or speed measuring means;
   wherein said data logger is configured for recording measurements from these measuring means as said cutting elements are pulled through soil.

4. A method for measuring variability in soil compaction with respect to depth, comprising:
   measuring soil resistance to cutting as a plurality of cutting elements are pulled through soil;
   maintaining a history of past measurements for a cultivated field; and
   comparing said measurements of soil resistance to cutting with said history of measurements for said cultivated field.

5. An apparatus as recited in claim 1, further comprising:
   a data logger;
   wherein said data logger is configured to record force measurements as said cutting elements are pulled through soil.

6. An apparatus as recited in claim 5:
   wherein said data logger comprises a programmable computer; and
   wherein said computer includes programming to record and analyze said force measurements.

7. An apparatus as recited in claim 6, further comprising:
   means for displaying said recorded and analyzed force measurements.

8. An apparatus as recited in claim 7, wherein said means for displaying said recorded and analyzed force measurements comprises an electronic display with a graphical user interface.

9. An apparatus as recited in claim 7, wherein said means for displaying said recorded and analyzed force measurements comprises a printer.

10. An apparatus as recited in claim 5, further comprising:
    a field position sensor coupled to said data logger.

11. A compaction profile sensing tine apparatus, comprising:
    a plurality of cutting elements;
    means for measuring force on each of the cutting elements as said cutting elements are pulled through soil,
    a data logger;
    wherein said data logger is configured to record force measurements as said cutting elements are pulled through soil; and
    a temperature sensor coupled to said data logger.

12. A compaction profile sensing tine apparatus, comprising:
    a plurality of cutting elements;
    means for measuring force on each of the cutting elements as said cutting elements are pulled through soil,
    a data logger;

wherein said data logger is configured to record force measurements as said cutting elements are pulled through soil; and a speed sensor coupled to said data logger.

13. A compaction profile sensing tine apparatus, comprising:

a plurality of cutting elements; and a plurality of independent load sensing elements;

each said load sensing element coupled to a corresponding cutting element;

each said load sensing element configured for measuring force on a corresponding cutting element as said cutting element is pulled through soil;

wherein said plurality of cutting elements form a cutting edge of a tine.

14. A compaction profile sensing tine apparatus, comprising:

a plurality of cutting elements;

a plurality of independent load sensing elements;

each said load sensing element coupled to a corresponding cutting element;

each said load sensing element configured for measuring force on a corresponding cutting element as said cutting element is pulled through soil; and a plurality of dummy cutting elements;

wherein said dummy cutting elements are configured for providing sufficient separation between adjacent cutting elements which have said load sensing elements;

wherein said dummy cutting elements reduce interference between adjacent load sensing elements toward providing accurate discrete soil layer measurements.

15. An apparatus as recited in claim 13, further comprising:

a tine body;

wherein said plurality of load sensing elements are coupled to said tine body.

16. An apparatus as recited in claim 13, further comprising:

a data logger;

wherein said data logger is configured to record force measurements as said cutting elements are pulled through soil.

17. An apparatus as recited in claim 16:

wherein said data logger comprises a programmable computer; and wherein said computer includes programming to record and analyze said force measurements.

18. An apparatus as recited in claim 17, further comprising:

means for displaying said recorded and analyzed force measurements.

19. An apparatus as recited in claim 18, wherein said means for displaying said recorded and analyzed force measurements comprises an electronic display with a graphical user interface.

20. An apparatus as recited in claim 18, wherein said means for displaying said recorded and analyzed force measurements comprises a printer.

21. An apparatus as recited in claim 16, further comprising:

a field position sensor coupled to said data logger.

a field position sensor coupled to said data logger.

22. A compaction profile sensing tine apparatus, comprising:

a plurality of cutting elements;

a plurality of independent load sensing elements;

each said load sensing element coupled to a corresponding cutting element;

each said load sensing element configured for measuring force on a corresponding cutting element as said cutting element is pulled through soil;

a data logger;

wherein said data logger is configured to record force measurements as said cutting elements are pulled through soil; and a temperature sensor coupled to said data logger.

23. A compaction profile sensing tine apparatus, comprising:

a plurality of cutting elements;

a plurality of independent load sensing elements;

each said load sensing element coupled to a corresponding cutting element;

each said load sensing element configured for measuring force on a corresponding cutting element as said cutting element is pulled through soil;

a data logger;

wherein said data logger is configured to record force measurements as said cutting elements are pulled through soil; and a speed sensor coupled to said data logger.

24. A compaction profile sensing tine apparatus, comprising:

a plurality of cutting elements;

said plurality of cutting elements forming a cutting edge of a tine; and a plurality of independent load sensing elements;

each said load sensing element coupled to a corresponding cutting element;

each said load sensing element configured for measuring force on a corresponding cutting element as said cutting element is pulled through soil.

25. An apparatus as recited in claim 24, further comprising:

a tine body;

wherein said plurality of load sensing elements are coupled to said tine body.

26. An apparatus as recited in claim 24, further comprising:

a data logger;

wherein said data logger is configured to record force measurements as said cutting elements are pulled through soil.

27. An apparatus as recited in claim 26:

wherein said data logger comprises a programmable computer; and wherein said computer includes programming to record and analyze said force measurements.

28. An apparatus as recited in claim 27, further comprising:

means for displaying said recorded and analyzed force measurements.

29. An apparatus as recited in claim 28, wherein said means for displaying said recorded and analyzed force measurements comprises an electronic display with a graphical user interface.

30. An apparatus as recited in claim 28, wherein said means for displaying said recorded and analyzed force measurements comprises a printer.

31. An apparatus as recited in claim 26, further comprising:
a field position sensor coupled to said data logger.

32. An apparatus as recited in claim 26, further comprising:
a temperature sensor coupled to said data logger.

33. An apparatus as recited in claim 26, further comprising:
a speed sensor coupled to said data logger.

34. A compaction profile sensing tine apparatus, comprising:
a tine body;
a plurality of independent load sensing elements coupled to said tine body;
a plurality of cutting elements forming a cutting edge of a tine;
each said cutting element coupled to a corresponding load sensing element;
each said load sensing element configured for measuring force on a corresponding cutting element as said cutting element is pulled through soil.

35. An apparatus as recited in claim 34, further comprising:
a data logger;
wherein said data logger is configured to record force measurements as said cutting elements are pulled through soil.

36. An apparatus as recited in claim 35:
wherein said data logger comprises a programmable computer; and
wherein said computer includes programming to record and analyze said force measurements.

37. An apparatus as recited in claim 36, further comprising:
means for displaying said recorded and analyzed force measurements.

38. An apparatus as recited in claim 37, wherein said means for displaying said recorded and analyzed force measurements comprises a electronic display with a graphical user interface.

39. An apparatus as recited in claim 37, wherein said means for displaying said recorded and analyzed force measurements comprises a printer.

40. An apparatus as recited in claim 24, further comprising:
a field position sensor.

41. An apparatus as recited in claim 35, further comprising:
a temperature sensor coupled to said data logger.

42. An apparatus as recited in claim 35, further comprising:
a speed sensor coupled to said data logger.

43. A method for measuring variability in soil compaction with respect to depth, comprising:
measuring soil resistance to cutting as a plurality of cutting elements are pulled through soil.

44. A method as recited in claim 43, further comprising:
measuring soil resistance to cutting at varying depths in a soil profile.

45. A method as recited in claim 44, further comprising:
computing a soil compaction index from said measurements of soil resistance to cutting at varying depths in a soil profile.

46. A method as recited in claim 43, further comprising:
recording said measurements of soil resistance to cutting within a soil profile; and
displaying said measurements of soil resistance to cutting at approximately the same time said measurements are recorded.

47. A method as recited in claim 43, further comprising:
recording said measurements of soil resistance to cutting within a soil profile; and
mapping said the measurements of soil resistance to cutting.

48. A method as recited in claim 43, further comprising:
recording location of said cutting elements within a field;
recording said measurements of soil resistance to cutting within a soil profile; and
mapping said the measurements of soil resistance to cutting according to said location of said cutting elements within said field.

49. A method as recited in claim 43, further comprising:
maintaining a history of past measurements for a cultivated field; and
comparing said measurements of soil resistance to cutting with said history of measurements for said cultivated field.

50. A method as recited in claim 49, wherein said history comprises:
crop chlorophyll content measurements;
cone index measurements; and
soil resistance to cutting measurements for said cultivated field.

51. A compaction profile sensing tine apparatus, comprising:
a plurality of cutting elements;
means for measuring force on each of the cutting elements as said cutting elements are pulled through soil; and
an overload protection device coupled to the combination of said cutting elements and said means for measuring force;
said overload protection device configured to prevent excessive cutting load forces from being applied from said cutting elements to said means for measuring force.

52. An apparatus as recited in claim 51:
wherein said cutting elements having said force measurement means are configured for being arranged in an approximate vertical orientation for cutting through the soil;
wherein said approximate vertical orientation can be on a slant in which said cutting elements are sequentially cutting through the same soil at different depths.

53. A compaction profile sensing tine apparatus, comprising:
a plurality of cutting elements;
means for measuring force on each of the cutting elements as said cutting elements are pulled through soil; and
a plurality of dummy cutting elements;
wherein said dummy cutting elements are configured for providing sufficient separation between adjacent cutting elements which have said force measuring means;
wherein said dummy cutting elements reduce interference between adjacent force measuring means toward providing accurate discrete soil layer measurements.

54. A compaction profile sensing tine apparatus, comprising:
- a plurality of cutting elements;
- a plurality of independent load sensing elements;
- each said load sensing element coupled to a corresponding cutting element;
- each said load sensing element configured for measuring force on a corresponding cutting element as said cutting element is pulled through soil; and
- an overload protection device coupled to the combination of said load sensing elements and said cutting elements;
- said overload protection device configured to prevent excessive cutting load forces from being applied from said cutting elements to said load sensing elements.

55. A compaction profile sensing tine apparatus, comprising:
- a plurality of cutting elements; and
- a plurality of independent load sensing elements;
- each said load sensing element coupled to a corresponding cutting elements;
- each said load sensing element configured for measuring force on a corresponding cutting element as said cutting element is pulled through soil;
- wherein said cutting elements having said load sensing elements are configured for being arranged in an approximate vertical orientation for cutting through the soil;
- wherein said approximate vertical orientation can be on a slant in which said cutting elements are sequentially cutting through the same soil at different depths.

56. An apparatus as recited in claim 24, further comprising:
- an overload protection device coupled to the combination of said load sensing elements and said cutting elements;
- said overload protection device configured to prevent excessive cutting load forces from being applied from said cutting elements to said load sensing elements.

57. An apparatus as recited in claim 24:
- wherein said cutting elements having said load sensing elements are configured for being arranged in an approximate vertical orientation for cutting through the soil;
- wherein said approximate vertical orientation can be on a slant in which said cutting elements are sequentially cutting through the same soil at different depths.

58. An apparatus as recited in claim 24, further comprising:
- a plurality of dummy cutting elements;
- wherein said dummy cutting elements are configured for providing sufficient separation between adjacent cutting elements which have said load sensing elements;
- wherein said dummy cutting elements reduce interference between adjacent load sensing elements toward providing accurate discrete soil layer measurements.

59. An apparatus as recited in claim 34, further comprising:
- an overload protection device coupled to each combination of said load sensing element and said cutting element;
- said overload protection device configured to prevent excessive cutting load forces from being applied from each of said cutting elements to each of said load sensing elements.

60. An apparatus as recited in claim 34:
- wherein said cutting elements having said load sensing elements are configured for being arranged in an approximate vertical orientation for cutting through the soil;
- wherein said approximate vertical orientation can be on a slant in which said cutting elements are sequentially cutting through the same soil at different depths.

61. An apparatus as recited in claim 34, further comprising:
- a plurality of dummy cutting elements;
- wherein said dummy cutting elements are configured for providing sufficient separation between adjacent cutting elements which have said load sensing elements;
- wherein said dummy cutting elements reduce interference between adjacent load sensing elements toward providing accurate discrete soil layer measurements.

62. A method as recited in claim 43, wherein said measuring is performed in response to data generated by a plurality of force sensors coupled to separate cutting elements along a cutting tine held in an approximate vertical orientation and configured for being pulled through the soil.

63. A method as recited in claim 62:
- wherein said cutting elements are interspersed with dummy cutting elements which cut but do not measure soil cutting resistance;
- wherein said dummy cutting elements reduce measurement interference between the cutting elements having force sensors.

* * * * *